United States Patent
Li et al.

(10) Patent No.: US 11,877,989 B2
(45) Date of Patent: Jan. 23, 2024

(54) NUTRITIONAL SUPPLEMENT CONTAINING L-α-GLYCEROPHOSPHORYLCHOLINE

(71) Applicant: Energy Beverages LLC, Corona, CA (US)

(72) Inventors: Liangxi Li, Plantation, FL (US); John H. Owoc, Southwest Ranches, FL (US)

(73) Assignee: Energy Beverages LLC, Corona, CA (US)

( * ) Notice: Subject to any disclaimer, the term of this patent is extended or adjusted under 35 U.S.C. 154(b) by 119 days.

(21) Appl. No.: 17/346,621

(22) Filed: Jun. 14, 2021

(65) Prior Publication Data

US 2021/0386692 A1      Dec. 16, 2021

Related U.S. Application Data

(60) Provisional application No. 63/038,403, filed on Jun. 12, 2020.

(51) Int. Cl.
| | |
|---|---|
| *A61K 31/14* | (2006.01) |
| *A61K 31/661* | (2006.01) |
| *A61K 31/522* | (2006.01) |
| *A61K 36/74* | (2006.01) |
| *A23L 33/00* | (2016.01) |
| *A23L 2/52* | (2006.01) |
| *A61K 9/00* | (2006.01) |
| *A61K 31/197* | (2006.01) |

(52) U.S. Cl.
CPC .............. *A61K 31/14* (2013.01); *A23L 2/52* (2013.01); *A23L 33/30* (2016.08); *A61K 9/0095* (2013.01); *A61K 31/197* (2013.01); *A61K 31/522* (2013.01); *A61K 31/661* (2013.01); *A61K 36/74* (2013.01)

(58) Field of Classification Search
CPC .... A61K 31/14; A61K 31/197; A61K 31/522; A61K 31/661
See application file for complete search history.

(56) References Cited

U.S. PATENT DOCUMENTS

2021/0169891 A1\* 6/2021 Lelah .................. A61K 31/522

OTHER PUBLICATIONS

Tinsley et al. Journal of the International Society of Sports Nutrition, 2017, 14:46, pp. 1-11 (Year: 2017).\*
Hoffman et al. Journal of the International Society of Sports Nutrition, 2010, 7:39, pp. 1-8 (Year: 2010).\*
Guest, N.S., et al., International society of sports nutrition position stand: caffeine and exercise performance. J Int Soc Sports Nutr, 2021. 18(1): p. 1.
Thakkar, D., et al., HFE Genotype and Endurance Performance in Competitive Male Athletes. Medicine & Science in Sports & Exercise: Jul. 2021—vol. 53—Issue 7—p. 1385-1390.
Antonio, J., et al., The Effects of an Energy Drink on Psychomotor Vigilance in Trained Individuals. J Funct Morphol Kinesiol, 2019. 4(3).
Magrini, M.A., et al., Effects of a Pre-workout Energy Drink Supplement on Upper Body Muscular Endurance Performance. Int J Exerc Sci, 2016. 9(5): p. 667-676.
Ivy, J.L., et al., Improved cycling time-trial performance after ingestion of a caffeine energy drink. Int J Sport Nutr Exerc Metab, 2009. 19(1): p. 61-78.
Del Coso, J., et al., Effects of a caffeine-containing energy drink on simulated soccer performance. PLOS One, 2012. 7(2): p. e31380.
Weintraub, S., et al., Cognition assessment using the NIH Toolbox. Neurology, 2013. 80(11 Suppl 3): p. S54-64.
Weintraub, S., et al., The cognition battery of the NIH toolbox for assessment of neurological and behavioral function: validation in an adult sample. J Int Neuropsychol Soc, 2014. 20(6): p. 567-78.
Jones, M.J., et al., The psychomotor vigilance test: a comparison of different test durations in elite athletes. J Sports Sci, 2018. 36(18): p. 2033-2037.
Cappelletti, S., et al., Caffeine: cognitive and physical performance enhancer or psychoactive drug? Curr Neuropharmacol, 2015. 13(1): p. 71-88.

\* cited by examiner

*Primary Examiner* — James D. Anderson
(74) *Attorney, Agent, or Firm* — Knobbe, Martens, Olson & Bear LLP (57) ABSTRACT

A nutritional supplement contains 50% to 80% by weight of trimethylglycine; 5% to 30% by weight of L-α-glycerophosphorylcholine; 5% to 15% by weight of caffeine; and 5% to 10% by weight of an ingredient selected from the group consisting of an L-amino acid, creatyl-L-leucine, *Corynanthe yohimbe* bark extract, theacrine, and mixtures thereof. The nutritional supplement is useful for enhancing energy, mental acuity, cognitive performance, and reaction time in a subject in need thereof.

17 Claims, 3 Drawing Sheets

NUTRITIONAL SUPPLEMENT CONTAINING L-α-GLYCEROPHOSPHORYLCHOLINE

TECHNICAL FIELD

The present disclosure relates generally to nutritional supplements for enhancing athletic performance, energy, mental acuity, and cognitive performance in a subject. More particularly, the disclosure relates nutritional supplements containing L-α-glycerophosphorylcholine.

BACKGROUND

Several studies have found that caffeine-containing energy drinks may enhance physical performance as well as cognitive function (Guest, 2021; Thakkar, 2022; Antonio, 2019; Magrini, 2016; Ivy, 2009; and Del Coso, 2012). A recent position stand from the International Society of Sports Nutrition states that the benefits of caffeine supplementation on exercise performance may occur when consumed in doses of 3-6 mg/kg body mass (Guest, 2021). A study consisting of 12 trained cyclists that consumed an energy drink containing 160 mg of caffeine or a placebo before a simulated cycling time trial found that subjects who consumed the energy drink improved their endurance performance (Ivy, 2009). Another study conducted on semi-professional soccer players found a caffeine-containing energy drink in a dose of 3 mg/kg of body mass increased the ability to repeatedly spring at high intensity during a simulated soccer game (Del Coso, 2012). In addition to physical performance, a recent investigation by Antonio et al. found that in healthy individuals, acute consumption of an energy drink at a caffeine dose of 4 mg/kg body mass improved cognitive function through a psychomotor vigilance test, which measured sustained attention (Antonio, 2019). Additionally, a recent study by Magrini et al. found that four ounces of Redline energy drink improved muscular endurance but did not provide any benefit over a placebo (Magrini, 2016).

The compound choline is a precursor of the neurotransmitter acetylcholine, which is associated with memory and learning. Much of the population is deficient in choline and would benefit from choline supplementation. Choline bitartrate is the cheapest form of choline, but this salt is very ineffective at crossing the blood-brain barrier. Improved nutritional supplements which deliver readily bioavailable forms of choline and choline precursors are needed. Choline supplementation may also enhance athletic performance.

Trimethylglycine (betaine anhydrous) also may enhance protein synthesis and improve body composition by reducing levels of homocysteine and homocysteine thiolactone.

In view of the foregoing, it would be desirable to develop improved nutritional supplements comprising a bioavailable choline precursor and trimethylglycine. In particular, it would be desirable to create such a formulation for simultaneously improving cognitive and athletic performance.

SUMMARY

In light of the present need for compositions for enhancing energy, mental acuity, cognitive performance, and reaction time in subjects in need thereof, a brief summary of various exemplary embodiments is presented. Some simplifications and omissions may be made in the following summary, which is intended to highlight and introduce some aspects of the various exemplary embodiments, but not to limit the scope of the invention. Detailed descriptions of an exemplary embodiments adequate to allow those of ordinary skill in the art to make and use the inventive concepts will follow in later sections.

Various embodiments disclosed herein relate to a nutritional supplement, including an effective amount of trimethylglycine, an effective amount of L-α-glycerophosphorylcholine, an effective amount of caffeine, and an effective amount of an ingredient selected from the group consisting of an L-amino acid, creatyl-L-leucine, *Corynanthe yohimbe* bark extract, theacrine, and mixtures thereof. In various embodiments, the ingredient contains creatyl-L-leucine. In various embodiments, the ingredient contains an L-amino acid which may be methionine, asparagine, glutamine, aspartic acid, glutamic acid, theanine, derivatives thereof, or a combination thereof. The nutritional supplement may be combined with a carrier. The carrier may be an aqueous carrier. The carrier may be an aqueous carrier comprising electrolyte salts. A composition may be a beverage including the nutritional supplement and an aqueous carrier.

Various embodiments disclosed herein relate to a nutritional supplement, including:
  an effective amount of trimethylglycine,
  an effective amount of L-α-glycerophosphorylcholine,
  an effective amount of caffeine, and
  an effective amount of an ingredient selected from the group consisting of an L-amino acid, creatyl-L-leucine, *Corynanthe yohimbe* bark extract, theacrine, and mixtures thereof;
  wherein L-α-glycerophosphorylcholine and caffeine are used in a ratio ranging from 1:1 to 2:1, from 1:1 to 4:3, or from 4:3 to 2:1.

In various embodiments, the ingredient contains creatyl-L-leucine. In various embodiments, the ingredient contains an L-amino acid which may be methionine, asparagine, glutamine, aspartic acid, glutamic acid, theanine, derivatives thereof, or a combination thereof.

The nutritional supplement may include an ingredient containing an L-amino acid selected from the group consisting of an N-alkyl derivative of asparagine, an N-alkyl derivative of glutamine, an alkyl ester of aspartic acid, an alkyl ester of glutamic acid, and combination thereof. In some embodiments, the ingredient contains $N^5$-ethyl-L-glutamine (L-theanine).

In various embodiments, the nutritional supplement contains 60% to 75% by weight of trimethylglycine and 10% to 20% by weight of L-α-glycerophosphorylcholine.

Various exemplary embodiments relate to a nutritional supplement, containing 50% to 80% by weight of trimethylglycine, 5% to 30% by weight of L-α-glycerophosphorylcholine (α-GPC, Formula I), 5% to 15% by weight of caffeine, and 5% to 10% by weight of an ingredient selected from the group consisting of an L-amino acid, creatyl-L-leucine, *Corynanthe yohimbe* bark extract, theacrine, and mixtures thereof. The nutritional supplement may contain 60% to 75% by weight of trimethylglycine and 10% to 20% by weight of L-α-glycerophosphorylcholine.

Formula I

In various embodiments, the nutritional supplement includes an ingredient containing L-theanine. The nutritional supplement may include an ingredient containing creatyl-L-leucine.

In various embodiments, the nutritional supplement includes an ingredient containing an L-amino acid selected from the group consisting of asparagine, glutamine, aspartic acid, glutamic acid, theanine, derivatives thereof, and combination thereof. The nutritional supplement may contain theanine.

Various embodiments disclosed herein relate to a dosage form containing a nutritional supplement including:
- 50% to 80% by weight of trimethylglycine,
- 5% to 30% by weight of L-α-glycerophosphorylcholine,
- 5% to 15% by weight of caffeine, and
- 5% to 10% by weight of an ingredient selected from the group consisting of an L-amino acid, creatyl-L-leucine, *Corynanthe yohimbe* bark extract, theacrine, and mixtures thereof. L-α-glycerophosphorylcholine and caffeine may be used in a ratio ranging from 1:1 to 2:1, from 1:1 to 4:3, or from 4:3 to 2:1. The dosage form may be a tablet, a capsule, a syrup, an emulsion, a dispersion, a candy, a liquid shot, or a carbonated or non-carbonated beverage.

Various embodiments disclosed herein relate to a method of enhancing energy, mental acuity, cognitive performance, and reaction time in a subject in need thereof, comprising administering an effective amount of a nutritional supplement to the subject, where the nutritional supplement includes:
- 50% to 80% by weight of trimethylglycine,
- 5% to 30% by weight of L-α-glycerophosphorylcholine,
- 5% to 15% by weight of caffeine, and
- 5% to 10% by weight of an ingredient selected from the group consisting of an L-amino acid, creatyl-L-leucine, *Corynanthe yohimbe* bark extract, theacrine, and mixtures thereof. The effective amount of the nutritional supplement may range from 1,500 mg/dose to 8,000 mg/dose, based on the total weight of the nutritional supplement. The effective amount of the nutritional supplement may be sufficient to provide the subject with L-α-glycerophosphorylcholine in an amount ranging from 100 mg/dose to 1,875 mg/dose.

Various embodiments disclosed herein relate to a method of enhancing pattern recognition skills and reaction time in a subject in need thereof, comprising administering an effective amount of a nutritional supplement to the subject, where the nutritional supplement includes:
- 50% to 80% by weight of trimethylglycine,
- 5% to 30% by weight of L-α-glycerophosphorylcholine,
- 5% to 15% by weight of caffeine, and
- 5% to 10% by weight of an ingredient selected from the group consisting of an L-amino acid, creatyl-L-leucine, *Corynanthe yohimbe* bark extract, theacrine, and mixtures thereof. The effective amount of the nutritional supplement ranges from 1,500 mg/dose to 8,000 mg/dose, based on the total weight of the nutritional supplement. The effective amount of the nutritional supplement is sufficient to provide the subject with L-α-glycerophosphorylcholine in an amount ranging from 100 mg/dose to 1,875 mg/dose.

Various embodiments relate to a dosage form including the nutritional supplement and a carrier. The dosage form may be a tablet, a capsule, a syrup, an emulsion, a dispersion, a candy, a liquid shot, a carbonated beverage, or a non-carbonated beverage. The carrier may be a liquid carrier or a solid carrier. The dosage form may be a beverage, and the liquid carrier may be a carbonated or non-carbonated aqueous carrier.

BRIEF DESCRIPTION OF THE DRAWINGS

In order to better understand various exemplary embodiments, reference is made to the accompanying drawings, wherein.

DETAILED DESCRIPTION

According to the foregoing, various exemplary embodiments provide for nutritional supplements containing trimethylglycine, L-α-glycerophosphorylcholine, caffeine, and an ingredient which may be an L-amino acid, creatyl-L-leucine, *Corynanthe yohimbe* bark extract, theacrine, or a mixture thereof.

Various embodiments disclosed herein relate to a nutritional supplement, including an effective amount of trimethylglycine (betaine anhydrous), an effective amount of L-α-glycerophosphorylcholine, an effective amount of caffeine, and an effective amount of an ingredient which may be an L-amino acid, creatyl-L-leucine, *Corynanthe yohimbe* bark extract, theacrine, or a mixture thereof, where the nutritional supplement comprises 60% to 75% by weight of trimethylglycine and 10% to 20% by weight of L-α-glycerophosphorylcholine.

A. L-Amino Acids

Suitable L-amino acids include alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, tyrosine, mixtures thereof, and derivatives thereof. In various embodiments, the nutritional supplement may include an amino acid containing methionine, asparagine, glutamine, aspartic acid, glutamic acid, mixtures thereof, or derivatives thereof. The nutritional supplement may include an N-alkyl derivative of asparagine, an N-alkyl derivative of glutamine, an alkyl ester of aspartic acid, an alkyl ester of glutamic acid, or a mixture thereof.

In some embodiments, the amino acid is $N^5$-ethyl-L-glutamine, also known as theanine. L-theanine and its effect on stress related symptoms and cognitive function have been studied. Cognitive function, including verbal fluency, improved for subjects taking L-theanine, compared to subjects taking a placebo. L-theanine stimulates alpha wave activity in the brain. Alpha waves are associated with a relaxed but alert mental state and may lead to the observed improvement in cognitive function.

B. L-α-Glycerophosphorylcholine (α-GPC)

As discussed above, the nutritional supplement includes an effective amount of L-α-glycerophosphorylcholine (α-GPC). α-GPC is a natural choline compound made up of choline and glycerophosphate. The compound α-GPC rapidly delivers choline across the blood-brain barrier and is a precursor of the neurotransmitter acetylcholine, which is associated with memory and learning. The compound α-GPC is readily absorbed through oral intake to form free choline and is able to increase both dopamine and serotonin concentrations in the frontal cortex and cerebellum.

The compound α-GPC is a semi-synthetic lecithin derivative. Following oral administration, it is converted to phosphatidylcholine, a metabolically active form of choline that increases acetylcholine synthesis and release. More particularly, α-GPC is metabolized to choline, with choline serving as substrate for renewed synthesis of phosphatidylcholine. Phosphatidylcholine may in turn be deacylated to produce α-GPC and two fatty acids. α-GPC may be converted into acetylcholine or into serine byway of trimethylglycine. See FIG. 1 for a summary of α-GPC metabolism.

A series of studies were conducted to demonstrate the safety of α-GPC. The oral LD50 was equal to or greater than 10,000 mg/kg in rats and mice. Sub-chronic and chronic oral toxicity studies in rats (up to 1000 mg/kg/day) and beagles (up to 300 mg/kg/day) produced symptomology primarily consisting of reduced activity; slight decreases in food consumption and body weight gain; and slight reduction in liver weight, paralleled by significant decreases in plasma triglycerides, bilirubin, and alkaline phosphatase. There were no histopathological correlates. The in vivo and in vitro assays indicated that α-GPC was devoid of mutagenic activity. Based on these results, α-GPC is not genotoxic in vitro or in vivo, and exhibits low acute oral toxicity.

The compound α-GPC has been shown to promote long-term brain health as well as attention and memory and has also been researched for its potential to remediate poor cognition as a result of stroke or neurodegeneration.

The compound α-GPC is approved as a dietary supplement component under provisions of the Dietary Supplement Health and Education Act of 1994 and is classified as generally recognized as safe (GRAS) according to FDA standards.

By some estimates, 90% of the U.S. population is deficient in choline. Choline bitartrate (41% choline) is the simplest, cheapest form of choline, but this form is very ineffective at crossing the blood-brain barrier. The compound α-GPC carries 40% choline, easily crosses the blood-brain barrier, and is a nootropic choline source.

The compound α-GPC is a cognitive enhancer whose mode of action is considered to involve the release of free choline, which is then utilized for acetylcholine and phosphatidylcholine biosynthesis in the brain. A single intramuscular dose of α-GPC was associated with a rapid rise in plasma choline, peak levels being observed within about half an hour after the injection. The concentration of choline returned to near baseline values over a six hour period.

When healthy male subjects ingested α-GPC in an amount of 1000 mg, plasma growth hormone secretion was increased significantly 60 min after taking α-GPC, when compared to subjects administered a placebo. In another study, subjects administered 600 mg per day of α-GPC exhibited increased lower body force production after 6 days of α-GPC supplementation.

When subjects ingested 600 mg α-GPC in a single dose, peak growth hormone levels increased 44-fold after α-GPC supplementation (from 0.19±0.06 to 8.4±2.1 ng/mL), vs. 2.6-fold after placebo supplementation. Peak bench press force was 14% greater in subjects administered 600 mg α-GPC. α-GPC at a dose of 6 mg/kg increases upper body power output by 12% and improves accuracy during a reaction-time test by 12%. α-GPC may serve as an ergogenic aid for physical or cognitive stimulation.

Oral α-GPC reverses amnesia caused by scopolamine in passive avoidance. The peak effect is observed using 600 mg/kg, 5 h before training. α-GPC is cleaved within the gut to glycerophosphate and free choline and may act by increasing levels of acetylcholine precursors.

α-GPC has been tested in patients after stroke or transient ischemic attacks. α-GPC was administered after an attack at a daily dose of 1000 mg for 28 days, and then at a dose of 400 mg three times per day for the next 5 months. α-GPC assists in the cognitive recovery of patients with acute stroke or transient ischemic attacks.

Figure 1:
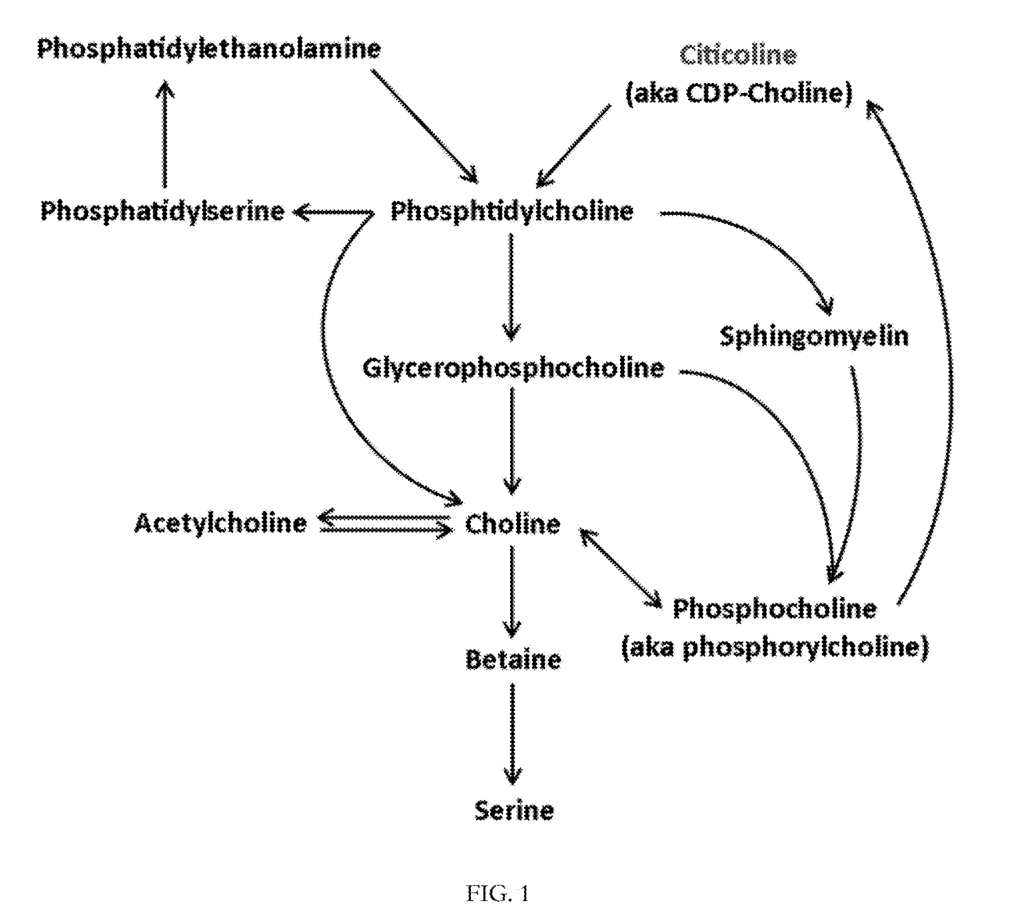
FIG. 1 shows a summary of L-α-glycerophosphorylcholine metabolism.

In some embodiments, an α-GPC precursor or prodrug may be used in place of α-GPC itself. Some suitable α-GPC precursors are shown in FIG. 1, including phosphatidylethanolamine, phosphatidylcholine, and citicoline.

C. Betaine Anhydrous

As also discussed above, the nutritional supplement includes an effective amount of trimethylglycine (betaine anhydrous). Trimethylglycine may function by donating a methyl group to transmethylate homocysteine (2-Amino-4-sulfanylbutanoic acid) back to methionine, increasing homocysteine metabolism and the availability of the universal methyl donor, S-adenosylmethionine. Trimethylglycine supplementation may enhance protein synthesis and improve body composition by reducing levels of homocysteine and homocysteine thiolactone. Six-weeks of trimethylglycine supplementation has been shown to improve body composition, arm size, and bench press work capacity, and to attenuate the rise in urinary homocysteine thiolactone (HCTL). Trimethylglycine supplementation tends to improve power, but not strength.

The combination of trimethylglycine, L-α-glycerophosphorylcholine, caffeine, and an amino acid, such as theanine, serves to enhance athletic performance while also enhancing mental acuity, cognitive performance, and reaction time in a subject in need thereof.

Various embodiments disclosed herein relate to a nutritional supplement, including:
  50% to 80% by weight, 55% to 78% by weight, 60% to 75% by weight, or 66% to 73% by weight of trimethylglycine;
  5% to 30% by weight, 8% to 25% by weight, 10% to 20% by weight, or 12% to 17% by weight of L-α-glycerophosphorylcholine;
  5% to 15% by weight, 6% to 12% by weight, 7% to 10% by weight, or 8% to 9% by weight of caffeine; and
  5% to 10% by weight of an ingredient selected from the group consisting of an L-amino acid, creatyl-L-leucine, *Corynanthe yohimbe* bark extract, theacrine, and mixtures thereof.

Various embodiments disclosed herein relate to a dosage form, including an effective amount of trimethylglycine (betaine anhydrous), an effective amount of L-α-glycerophosphorylcholine, an effective amount of caffeine, and an effective amount of an ingredient which may be an L-amino acid, creatyl-L-leucine, *Corynanthe yohimbe* bark extract, theacrine, or a mixture thereof. The dosage form may be a tablet, a capsule, a syrup, an emulsion, a dispersion, a candy, a liquid shot, or a carbonated or non-carbonated beverage. The dosage form may be a sports drink containing electrolyte salts. Suitable electrolytes may include soluble salts of sodium, potassium, calcium, magnesium, chloride, phosphate, carbonate, and/or bicarbonate.

Various embodiments disclosed herein relate to a dosage form, including:
  from 1,000 mg/dose to 5,000 mg/dose, from 1,500 mg/dose to 4,000 mg/dose, from 2,000 mg/dose to 3,000 mg/dose, or about 2,500 mg/dose of trimethylglycine;

from 100 mg/dose to 1,875 mg/dose, from 200 mg/dose to 1,200 mg/dose, from 300 mg/dose to 900 mg/dose, or from 400 mg/dose to 600 mg/dose of L-α-glycerophosphorylcholine;

from 100 mg/dose to 900 mg/dose, from 200 mg/dose to 700 mg/dose, from 250 mg/dose to 500 mg/dose, or about 300 mg/dose of caffeine; with the balance being an ingredient selected from the group consisting of an L-amino acid, creatyl-L-leucine, *Corynanthe yohimbe* bark extract, theacrine, and mixtures thereof.

The dosage forms disclosed herein may be administered to a subject in need thereof from one to three times per day, as needed. The effective amount of the nutritional supplement may range from 1,500 mg/dose to 8,000 mg/dose, based on the total weight of the composition.

The nutritional supplements may include an amino acid containing methionine, asparagine, glutamine, aspartic acid, glutamic acid, mixtures thereof, or derivatives thereof. The amino acid may be an N-alkyl derivative of asparagine, an N-alkyl derivative of glutamine, an alkyl ester of aspartic acid, an alkyl ester of glutamic acid, or a mixture thereof. In some embodiments, the amino acid $N^5$-ethyl-L-glutamine, or theanine. Theanine stimulates alpha wave function and improves cognitive performance, as discussed above.

The nutritional supplements disclosed herein may include creatyl-L-leucine. Creatyl-L-leucine is a dipeptide that is more soluble than either creatine or L-leucine and may serve as a soluble source of creatine and leucine. Creatine and leucine serve to increase muscle hypertrophy, muscle strength, muscle repair, muscle energetics, muscle protein synthesis, anabolism, and also to inhibit myostatin, preventing muscle protein breakdown.

In various embodiments, the nutritional supplements disclosed herein may include *Corynanthe yohimbe* bark extract, which contains yohimbine. Yohimbine increases adrenaline levels in the body and stimulates fat burning. Thus, *Corynanthe yohimbe* bark extract may stimulate athletic performance during training.

The nutritional supplements disclosed herein may include theacrine. Theacrine is related to caffeine, and may stimulate improved cognitive performance, energy, and mood.

The nutritional supplement disclosed herein may be administered to a subject in need of enhancing cognitive performance. The subject may have experienced cognitive deficits in the wake of a stroke, a transient is chemic event, or a neurodegenerative disorder such as Alzheimer's disease, or Pick's disease. From one to three doses of the nutritional supplement may be administered to the subject each day, where each dose may contain from 1,000 mg to 5,000 mg trimethylglycine, from 100 mg to 1,875 mg L-α-glycerophosphorylcholine, from 100 mg to 900 mg caffeine, and an effective amount of at least one of an L-amino acid, creatyl-L-leucine, *Corynanthe yohimbe* bark extract, and theacrine.

The impact of the nutritional supplement on cognitive performance may be assessed by periodic administration of a standard test for cognitive performance. Such tests are designed to measure mental functions, such as memory, language, and the object recognition. Typical tests include:
Montreal Cognitive Assessment (MoCA) test, which involves memorizing a short list of words, identifying a picture of an animal, and copying a drawing of a shape or object;
Mini-Mental State Exam (MMSE), which involves naming the current date, counting backward, and identifying everyday objects; and
Mini-Cog, which involves recalling a three-word list of objects and drawing a clock.

The nutritional supplement disclosed herein may be administered to a student, athlete, or other subject desiring increased alertness, focus, or reaction time. Changes in alertness or reaction time may be assessed with a Go/No-go test. Go/No-go tests may require a subject to perform an action under specific conditions, and retrain from performing that action under different conditions. Go/No-go tests are used in psychology to measure a participant's capacity for sustained attention, i.e., alertness. Video game performance or other activities that require rapid reaction time may also be used to assess changes in reaction time.

As discussed above, trimethylglycine supplementation may enhance protein synthesis and improve body composition in a subject. As also discussed above, α-GPC increases peak bench press force and upper body power output, and improves accuracy during a reaction-time test. Therefore, a subject administered the nutritional supplement disclosed herein may experience improved athletic performance, as well as improved alertness and/or reaction time.

Example 1. Nutritional Supplement

The table below presents a formulation for a nutritional supplement according to the present disclosure. The formulation includes trimethylglycine, α-GPC, and caffeine. The formulation also includes L-theanine, creatyl-L-leucine, *Corynanthe yohimbe* bark extract, and theacrine in a total amount of 232 mg.

| Ingredient | Amount (mg) | Amount (%) |
|---|---|---|
| trimethylglycine | 2,500 | 68.83 |
| L-α-glycerophosphorylcholine | 600 | 16.52 |
| caffeine | 300 | 8.26 |
| L-theanine | 58 | 1.60 |
| creatyl-L-leucine | 58 | 1.60 |
| *Corynanthe yohimbe* bark extract | 58 | 1.60 |
| theacrine | 58 | 1.60 |
| TOTAL | 3,632 | 100 |

Example 2. Nutritional Supplement

The table below presents a formulation for a nutritional supplement according to the present disclosure. The formulation includes L-theanine.

| Ingredient | Amount (mg) | Amount (%) |
|---|---|---|
| trimethylglycine | 2,500 | 72.8 |
| L-α-glycerophosphorylcholine | 400 | 11.7 |
| caffeine | 300 | 8.74 |
| L-theanine | 232 | 6.76 |
| TOTAL | 3,432 | 100 |

Example 3. Sports Drink

The table below presents a formulation for a 12 ounce (355 ml) serving of a sports drink containing a formulation according to the present disclosure. The formulation also includes L-theanine, creatyl-L-leucine, *Corynanthe yohimbe* bark extract, and/or theacrine in a total amount of 232 mg. Percentages are based on the weight of the nutritional supplement.

| Ingredient | Amount (mg) | Amount (%) |
| --- | --- | --- |
| Trimethylglycine | 2,500 | 68.8 |
| α-GPC | 600 | 16.5 |
| Caffiene | 300 | 8.25 |

Example 4. Sports Drink

The table below presents a formulation for a 12 ounce (355 ml) serving of a sports drink containing a nutritional supplement according to the present disclosure. The formulation also includes L-theanine, creatyl-L-leucine, *Corynanthe yohimbe* bark extract, and/or theacrine in a total amount of 232 mg. Percentages are based on the weight of the nutritional supplement.

| Ingredient | Amount (mg) | Amount (%) |
| --- | --- | --- |
| Trimethylglycine | 2,500 | 72.8 |
| α-GPC | 400 | 11.6 |
| Caffiene | 300 | 8.74 |

Example 5. Energy Drink

The table below presents a formulation for a 12 ounce (355 ml) serving of a sports drink containing a nutritional supplement according to the present disclosure.

| Ingredient | Amount (mg) | Amount (wt. %) |
| --- | --- | --- |
| trimethylglycine | 2,500 | 69.7 |
| L-α-glycero-phosphorylcholine | 400 | 11.1 |
| caffeine | 300 | 8.4 |
| Yohimbine HCl | 5 | 0.14 |
| L-Theanine | 200 | 5.6 |
| Theacrine | 2.5 | 0.07 |
| Creatyl-L-Leucine | 25 | 0.7 |
| Calcium (as $CaCl_2$) | 10 | 0.28 |
| Magnesium (as magnesium citrate) | 4 | 0.11 |
| Sodium (as $Na_3$ citrate) | 89 | 2.5 |
| Potassium (as $K_3$ citrate monohydrate) | 51 | 1.4 |

Example 6. Effects of an Energy Drink on Performance

Methods

A total of 12 exercise-trained men (n=3) and women (n=9) volunteered for a randomized, double-blind, placebo-controlled, crossover, counterbalanced trial. Subjects came to the clinical research site on two occasions separated by at least 3 days. Body composition of the subjects was assessed with a multi-frequency bioelectrical impedance device to determine each subject's physical characteristics.

Figure 2:
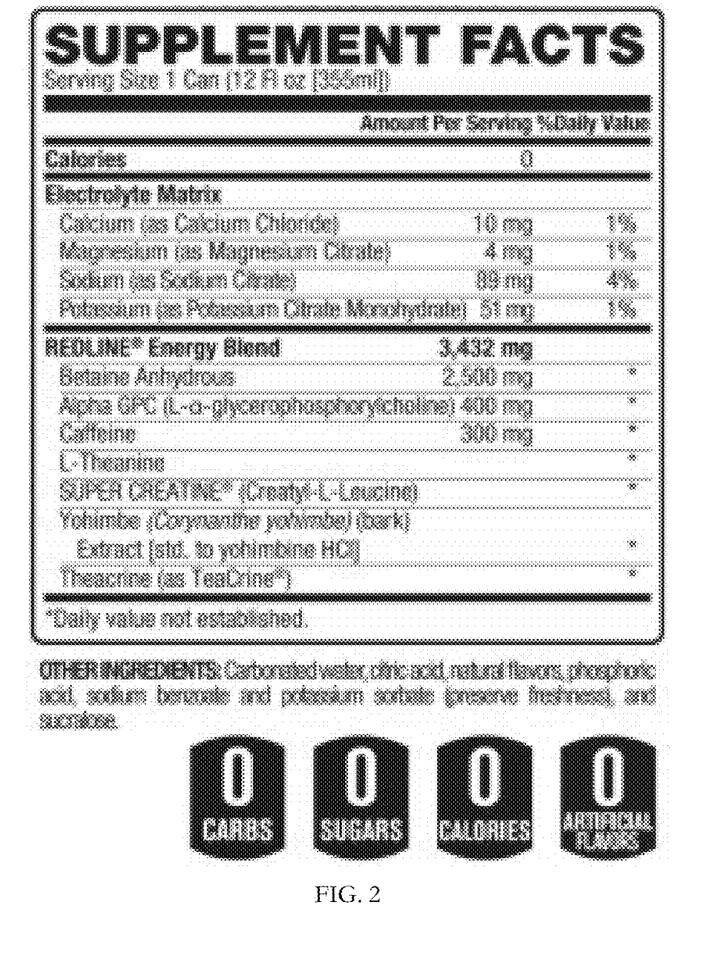
FIG. 2 shows ingredients of a formulation according to the present disclosure.

Subjects came to the lab on two occasions separated by one week between 1200 and 1700 hours. They consumed either an energy drink or a placebo in a randomized counterbalanced order. The composition of the energy drink is shown in FIG. 2.

Thirty to 45 minutes post-consumption, the subjects performed the following tasks of sustained attention and cognition:

5-minute psychomotor vigilance test (PVT);
the Flanker Inhibitory Control and Attention Test;
Dimensional Card Sort Test, and
Pattern Comparison Processing Speed Test (Weintraub, 2013; Weintraub, 2014).

The Flanker Inhibitory Control and Attention Test require that the study participant focus on a specific stimulus (e.g., the direction of the middle arrow in a set of three arrows) while ignoring the arrows that flank it. The study participant will then choose the correct direction of the middle arrow.

The Dimensional Card Sort Test requires that the study participant choose the correct color or shape depending on which variable the test is alluding to.

The Pattern Comparison Processing Speed Test serves as a measure of pattern recognition skills, and requires that the study participant distinguish between objects that are identical or not. It can be based on color, the addition/removal of an object, or the number of objects in a picture.

The psychomotor vigilance test is used to assess sustained-attention and reaction time (Jones, 2018; Antonio, 2019). Participants are instructed to respond to the sudden appearance of stimuli inside a box (i.e., numbers will appear at random times) by tapping the box as quickly as possible (i.e., reaction time) and avoid responding prematurely (i.e., false starts). This test lasts five minutes.

After completing the cognitive tasks, each subject ran to volitional exhaustion on a treadmill. Male and female subjects started at 7 and 6 miles per hour at 0% grade, respectively. Each minute the grade increased by 1%.

The energy drink and placebo were provided by VPX (Weston, FL USA). The active ingredient in the energy drink includes caffeine (300 mg per can [355 mL]); betaine (2,500 mg per can); and alpha glycerylphosphorylcholine (400 mg per can). The placebo and the energy drink were flavored similarly; however, the placebo did not contain caffeine, glycerylphosphorylcholine, or betaine.

All data is presented as the mean±SD. GraphPad (Prism 6) software was used for statistical analyses. A paired t-test and the Wilcoxon matched-pairs signed rank test was used to assess the differences between the treatment and placebo group for the cognitive tests as well as the treadmill run to exhaustion.

Results

Twelve exercise-trained men (n=3) and women (n=9) (mean±SD: age 25±5 years; height 1.66±0.08 meters; weight; 69.4±12.3 kilograms; % body fat 21.4±5.1%; daily caffeine intake 194±144 milligrams; mean hours per week of aerobic training 5.1±2.9; mean hours per week of resistance training 3.3±1.5) volunteered for this investigation. Each person consumed either the energy drink or the placebo.

Figure 3:
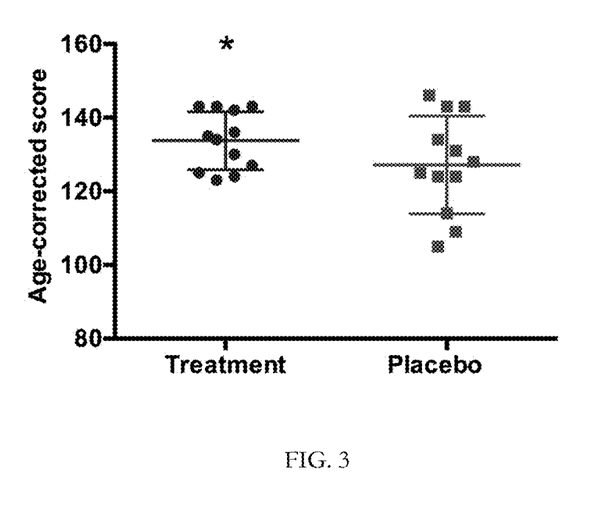
FIG. 3 shows the influence of a formulation according to the present disclosure on a Pattern Comparison Processing Speed Test.

Thirty to 45 minutes post-consumption, the subjects performed a Pattern Comparison Processing Speed Test. A significantly higher score was observed for subjects who consumed the energy drink than for subjects who consumed the placebo (p=0.03), as shown in Table 1 and FIG. 3.

Figure 4:
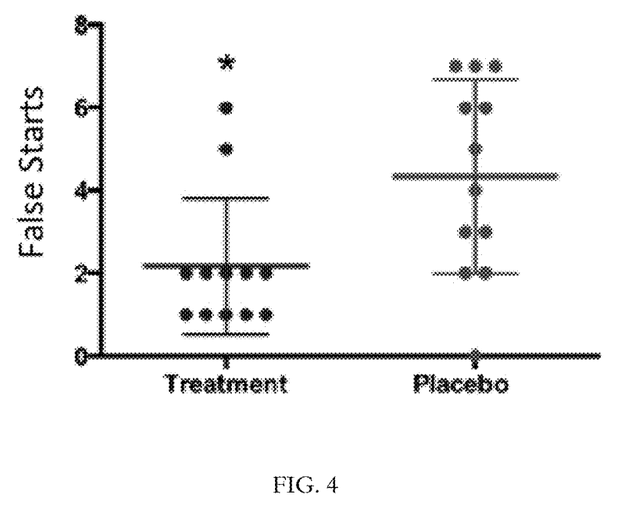
FIG. 4 shows the influence of a formulation according to the present disclosure on the number of false starts in a 5-minute psychomotor vigilance test (PVT).

Thirty to 45 minutes post-consumption, the subjects performed a 5-minute psychomotor vigilance test (PVT). No significant difference in psychomotor vigilance was observed between subjects who consumed the energy drink and subjects who consumed the placebo (p=0.66), as shown in Table 1. However, as shown in Table 1 and FIG. 4, the number of false starts during the PVT test was less in the energy drink group than in the placebo group (p=0.03).

Thirty to 45 minutes post-consumption, the subjects performed a Flanker Inhibitory Control and Attention Test. No significant difference in test results was observed between subjects who consumed the energy drink and subjects who consumed the placebo (p=0.19), as shown in Table 1.

There were no significant differences between subjects who consumed the energy drink and subjects who consumed the placebo for the Dimensional Card Sort Test (p=0.93), or for the time to exhaustion on the treadmill (p=0.54).

The results shown in Table 1 suggest that an energy drink containing trimethylglycine, L-α-glycerophosphorylcholine, and caffeine may promote improvements in sustained attention, e.g., pattern recognition, as well as measures of cognition.

TABLE 1

Cognitive and Physical Performance

| | Energy Drink | Placebo Drink | p value |
|---|---|---|---|
| Flanker Inhibitory Control and Attention Test | 112 ± 13 | 119 ± 19 | 0.19 |
| Dimensional Change Card Sort Test | 121 ± 12 | 122 ± 17 | 0.93 |
| Pattern Comparison Processing Speed Test | 134 ± 8* | 127 ± 13 | 0.03 |
| Psychomotor Vigilance Test (msec) | 288 ± 20 | 285 ± 25 | 0.66 |
| False Starts on the PVT Test | 2.2 ± 1.6* | 4.3 ± 2.4 | 0.03 |
| Time to Exhaustion (minutes) | 7.09 ± 3.04 | 7.36 ± 3.07 | 0.54 |

Data are expressed as the mean ± SD.
Legend: msec—millisecond; PVT—psychomotor vigilance test.
*Denotes differences that are statistically significant It is surprising that a formulation containing trimethylglycine, L-α-glycerophosphorylcholine, and caffeine leads to a reduction in false starts on the PVT test. Caffeine can increase arousal, and high doses of caffeine can increase feelings of anxiety and nervousness. (Guest, 2021; Cappelletti, 2015). Heightened feelings of anxiety and jitteriness from caffeine consumption would normally cause an increase in false starts on the PVT test. It appears that trimethylglycine and L-α-glycerophosphorylcholine may offset caffeine-induced nervousness, leading to a reduction in false starts. Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

REFERENCES

1. Guest, N. S., et al., *International society of sports nutrition position stand: caffeine and exercise performance*. J Int Soc Sports Nutr, 2021. 18(1): p. 1.
2. Thakkar, D., et al., *HEFE Genotype and Endurance Performance in Competitive Male Athletes*. Med Sci Sports Exerc, 2020. Publish Ahead of Print.
3. Antonio, J., et al., *The Effects of an Energy Drink on Psychomotor Vigilance in Trained Individuals*. J Funct Morphol Kinesiol, 2019. 4(3).
4. Magrini, M. A., et al., *Effects of a Pre-workout Energy Drink Supplement on Upper Body Muscular Endurance Performance*. Int J Exerc Sci, 2016. 9(5): p. 667-676.
5. Ivy, J. L., et al., *Improved cycling time-trial performance after ingestion of a caffeine energy drink*. Int J Sport Nutr Exerc Metab, 2009. 19(1): p. 61-78.
6. Del Coso, J., et al., *Effects of a caffeine-containing energy drink on simulated soccer performance*. PLoS One, 2012. 7(2): p. e31380.
7. Weintraub, S., et al., *Cognition assessment using the NIH Toolbox*. Neurology, 2013. 80(11 Suppl 3): p. S54-64.
8. Weintraub, S., et al., *The cognition battery of the NIH toolbox for assessment of neurological and behavioral function: validation in an adult sample*. J Int Neuropsychol Soc, 2014. 20(6): p. 567-78.
9. Jones, M. J., et al., *The psychomotor vigilance test: a comparison of different test durations in elite athletes*. J Sports Sci, 2018. 36(18): p. 2033-2037.
10. Cappelletti, S., et al., *Caffeine: cognitive and physical performance enhancer or psychoactive drug?* Curr Neuropharmacol, 2015. 13(1): p. 71-88.

What is claimed is:

1. A nutritional supplement, comprising:
   a. 50% to 80% by weight of trimethylglycine;
   b. 5% to 30% by weight of L-α-glycerophosphorylcholine or a precursor thereof, wherein the precursor is phosphatidylethanolamine, phosphatidylcholine, or citicoline;
   c. 5% to 15% by weight of caffeine; and
   d. 5% to 10% by weight of an ingredient selected from the group consisting of an L-amino acid, creatyl-L-leucine, *Corynanthe yohimbe* bark extract, theacrine, and mixtures thereof.

2. The nutritional supplement of claim 1, wherein the ingredient contains creatyl-L-leucine.

3. The nutritional supplement of claim 1, wherein the ingredient contains an L-amino acid selected from the group consisting of asparagine, glutamine, aspartic acid, glutamic acid, theanine, and combination thereof.

4. The nutritional supplement of claim 3 wherein the L-amino acid is L-theanine.

5. The nutritional supplement of claim 1, wherein the ingredient contains an L-amino acid selected from the group consisting of N-alkyl derivatives of asparagine, N-alkyl derivatives of glutamine, and combination thereof.

6. The nutritional supplement of claim 5, wherein the ingredient contains $N^5$-ethyl-L-glutamine.

7. The nutritional supplement of claim 1, wherein the nutritional supplement comprises 60% to 75% by weight of trimethylglycine and 10% to 20% by weight of L-α-glycerophosphorylcholine.

8. A dosage form comprising the nutritional supplement of claim 1 and a carrier.

9. The dosage form of claim 8, wherein the dosage form is a tablet, a capsule, a syrup, an emulsion, a dispersion, a candy, a liquid shot, a carbonated beverage, or a non-carbonated beverage.

10. The dosage form of claim 8, wherein the carrier is a liquid carrier or a solid carrier.

11. The dosage form of claim 8, wherein the dosage form is a beverage, and the carrier is a carbonated or non-carbonated aqueous carrier.

12. A method of enhancing energy, mental acuity, cognitive performance, and reaction time in a subject in need thereof, comprising administering an effective amount of the nutritional supplement of claim 11 to the subject.

13. The method of claim 12 wherein the effective amount of the nutritional supplement ranges from 1,500 mg/dose to 8,000 mg/dose, based on the total weight of the nutritional supplement.

14. The method of claim 12, wherein the effective amount of the nutritional supplement is sufficient to provide the subject with L-α-glycerophosphorylcholine in an amount ranging from 100 mg/dose to 1,875 mg/dose.

15. A method of enhancing pattern recognition skills and reaction time in a subject in need thereof, comprising administering an effective amount of the nutritional supplement of claim 1 to the subject.

16. The method of claim 15 wherein the effective amount of the nutritional supplement ranges from 1,500 mg/dose to 8,000 mg/dose, based on the total weight of the nutritional supplement.

17. The method of claim 16, wherein the effective amount of the nutritional supplement is sufficient to provide the subject with L-α-glycerophosphorylcholine in an amount ranging from 100 mg/dose to 1,875 mg/dose.

* * * * *

UNITED STATES PATENT AND TRADEMARK OFFICE
CERTIFICATE OF CORRECTION

PATENT NO. : 11,877,989 B2
APPLICATION NO. : 17/346621
DATED : January 23, 2024
INVENTOR(S) : Liangxi Li et al.

Page 1 of 1

It is certified that error appears in the above-identified patent and that said Letters Patent is hereby corrected as shown below:

In the Specification

Column 11, Line 59, delete "HEFE" and insert -- HFE --.

In the Claims

Column 12, Line 63, Claim 12, delete "11" and insert -- 1 --.

Signed and Sealed this
Fifteenth Day of July, 2025

Coke Morgan Stewart
*Acting Director of the United States Patent and Trademark Office*